United States Patent
Angibaud

(10) Patent No.: US 11,712,350 B2
(45) Date of Patent: Aug. 1, 2023

(54) DEVICES AND METHODS TO PREVENT JOINT INSTABILITY FOLLOWING ARTHROPLASTY

(71) Applicant: Exactech, Inc., Gainesville, FL (US)

(72) Inventor: Laurent Angibaud, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 104 days.

(21) Appl. No.: 16/324,015

(22) PCT Filed: Aug. 9, 2017

(86) PCT No.: PCT/US2017/046099
§ 371 (c)(1),
(2) Date: Feb. 7, 2019

(87) PCT Pub. No.: WO2018/031659
PCT Pub. Date: Feb. 15, 2018

(65) Prior Publication Data
US 2019/0167447 A1    Jun. 6, 2019

Related U.S. Application Data

(60) Provisional application No. 62/372,487, filed on Aug. 9, 2016.

(51) Int. Cl.
*A61B 17/02* (2006.01)
*A61F 2/46* (2006.01)
(Continued)

(52) U.S. Cl.
CPC .......... *A61F 2/4657* (2013.01); *A61B 5/1036* (2013.01); *A61B 5/1076* (2013.01);
(Continued)

(58) Field of Classification Search
CPC ................ A61B 2017/0268; A61F 2002/4666
See application file for complete search history.

(56) References Cited

U.S. PATENT DOCUMENTS

| | | | |
|---|---|---|---|
| 7,708,741 B1 | 5/2010 | Bonutti | |
| 2003/0187452 A1* | 10/2003 | Smith | ................. A61B 17/155 606/88 |

(Continued)

FOREIGN PATENT DOCUMENTS

| | | |
|---|---|---|
| JP | 2001-522286 A | 11/2001 |
| JP | 2004-249102 A | 9/2004 |

(Continued)

OTHER PUBLICATIONS

International Search Report and Written Opinion issued in International Application No. PCT/US2017/046099 dated Oct. 20, 2017.

(Continued)

*Primary Examiner* — Nicholas W Woodall
(74) *Attorney, Agent, or Firm* — Greenberg Traurig, LLP

(57) ABSTRACT

A kit includes a distractor, a plurality of trial elements, and at least one sensor. The distractor is configured to separate a first bone from a second bone by adjusting the distance between a first member and a second member, and is configured to receive at least one sensor in the first portion. Each of the trial elements corresponds to one of a plurality of surgical implants, is configured to be temporarily coupled to the second bone so as to evaluate suitability of the corresponding one of the plurality of surgical implants for implantation, and is configured to receive at least one sensor. The at least one sensor is configured to be received in the distractor or one of the trial elements, and is configured to record a magnitude of a force, a direction of application of a force, a pressure mapping, or a location of application of a force.

18 Claims, 14 Drawing Sheets

(51) Int. Cl.
    *A61F 2/38*     (2006.01)
    *A61B 5/107*     (2006.01)
    *A61B 5/00*     (2006.01)
    *A61B 5/103*     (2006.01)
    *A61F 2/30*     (2006.01)
    *A61B 34/10*     (2016.01)
    *A61B 17/00*     (2006.01)
    *A61B 34/20*     (2016.01)
    *A61B 90/00*     (2016.01)

(52) U.S. Cl.
    CPC .......... *A61B 5/4585* (2013.01); *A61B 17/025* (2013.01); *A61F 2/389* (2013.01); *A61F 2/3859* (2013.01); *A61F 2/461* (2013.01); *A61F 2/4684* (2013.01); *A61B 2017/00075* (2013.01); *A61B 2017/0268* (2013.01); *A61B 2034/105* (2016.02); *A61B 2034/2051* (2016.02); *A61B 2090/064* (2016.02); *A61F 2002/30125* (2013.01); *A61F 2002/30148* (2013.01); *A61F 2002/30153* (2013.01); *A61F 2002/30154* (2013.01); *A61F 2002/30616* (2013.01); *A61F 2002/4632* (2013.01); *A61F 2002/4658* (2013.01); *A61F 2002/4666* (2013.01); *A61F 2002/4668* (2013.01)

(56) References Cited

U.S. PATENT DOCUMENTS

| | | | |
|---|---|---|---|
| 2004/0064073 A1* | 4/2004 | Heldreth | A61F 2/4684 600/595 |
| 2004/0193286 A1 | 9/2004 | Grundei | |
| 2006/0149277 A1* | 7/2006 | Cinquin | A61B 17/025 606/90 |
| 2010/0249658 A1 | 9/2010 | Sherman et al. | |
| 2010/0250284 A1 | 9/2010 | Roche et al. | |
| 2010/0250571 A1* | 9/2010 | Pierce | G16H 70/60 707/758 |
| 2013/0226034 A1 | 8/2013 | Stein et al. | |
| 2013/0261631 A1* | 10/2013 | Ruhling | A61B 17/025 606/90 |
| 2015/0105782 A1 | 4/2015 | D'Lima et al. | |
| 2016/0278754 A1* | 9/2016 | Todorov | A61B 17/025 |
| 2018/0177607 A1* | 6/2018 | Trabish | A61B 34/10 |

FOREIGN PATENT DOCUMENTS

| | | |
|---|---|---|
| JP | 2014-531930 A | 12/2014 |
| WO | 98/48740 A1 | 11/1998 |
| WO | 2011/127477 A1 | 10/2011 |
| WO | 2013/044117 A1 | 3/2013 |

OTHER PUBLICATIONS

Gabay, "Fundamentals of Piezoelectric Shock and Vibration Sensors", DigiKey Electronics, Dec. 2011, retrieved Sep. 28, 2017 <<https://web.archive.org/web/20160715230901/https://www.digikey.com/en/articles/techzone/2011/dec/fundamentals-of-piezoelectric-shock-and-vibration-sensors>>.

* cited by examiner

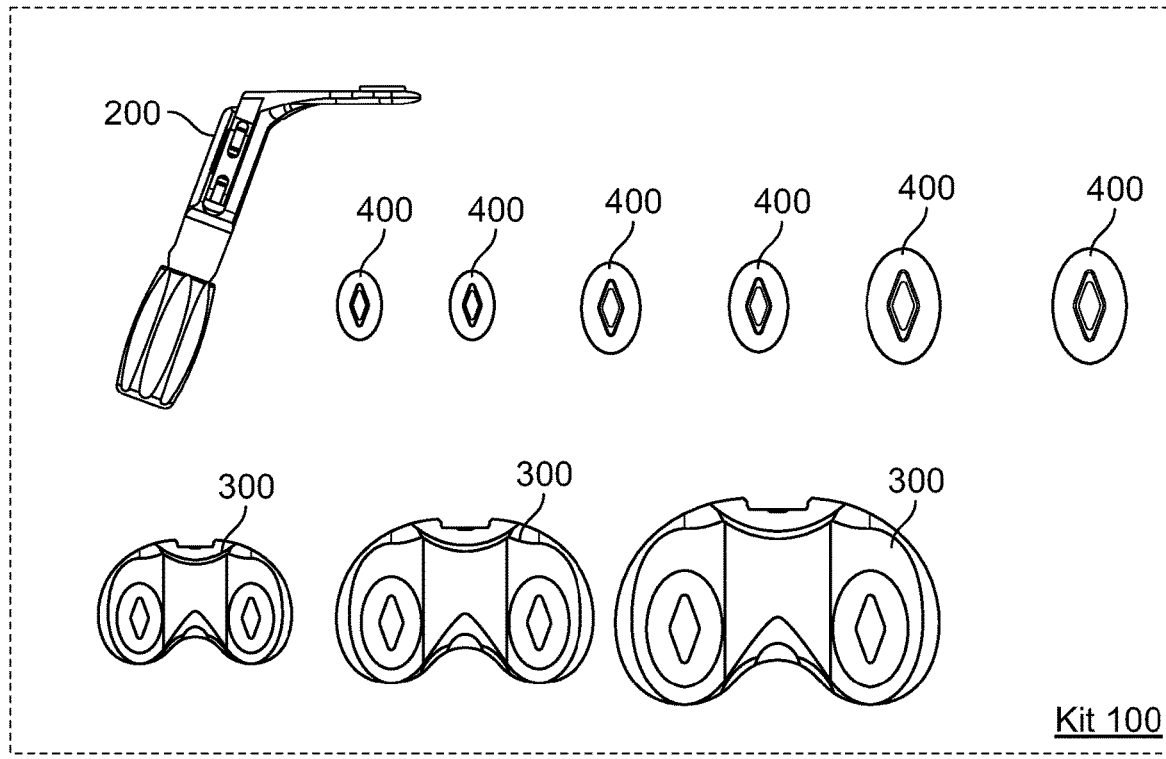
Figure 1
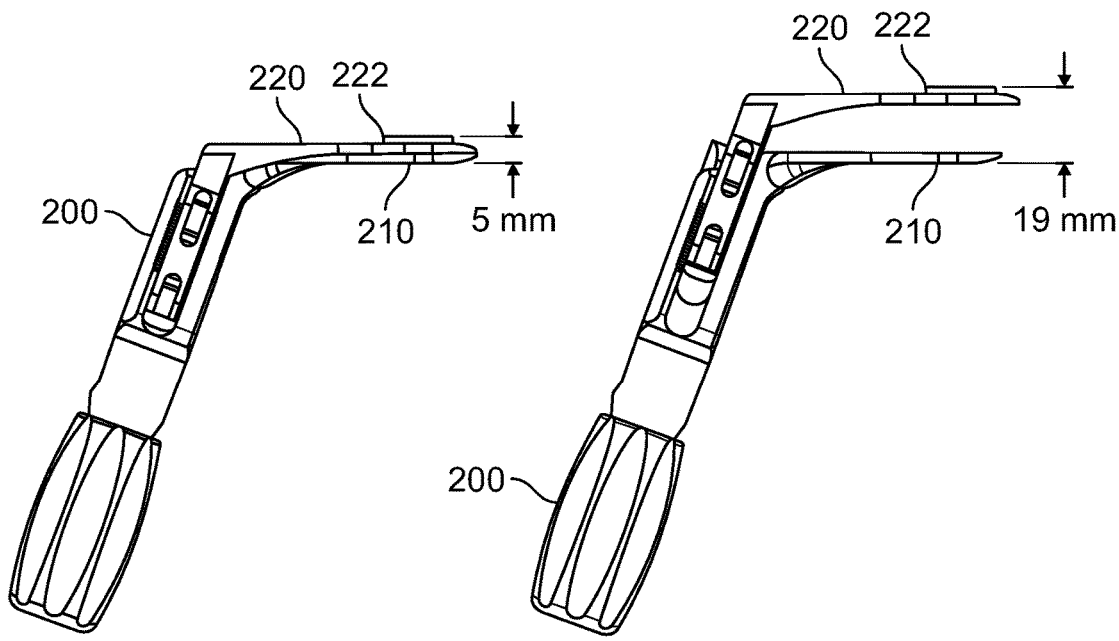
Figure 2A
Figure 2B

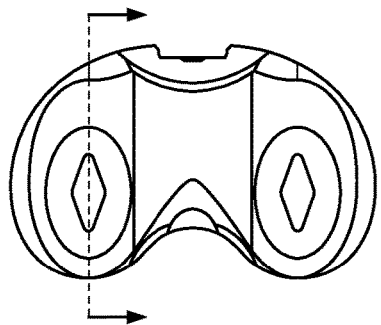
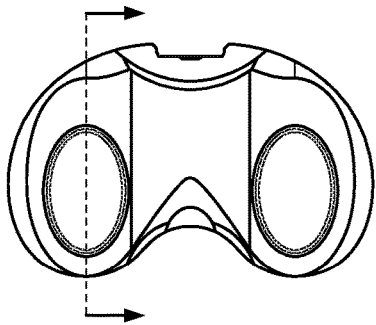
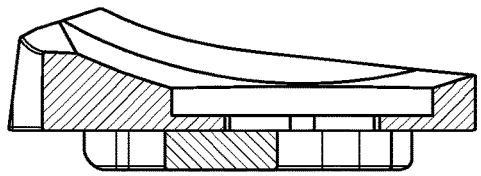
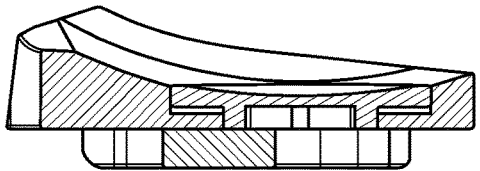
Figure 15A
Figure 15B
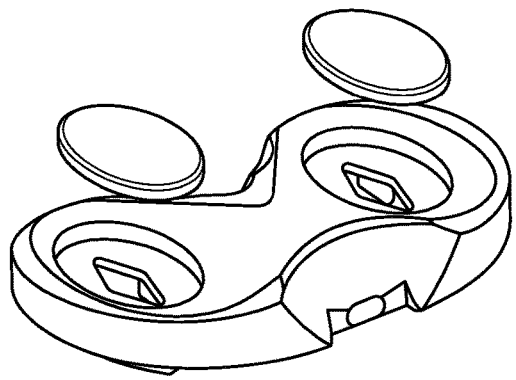
Figure 15C
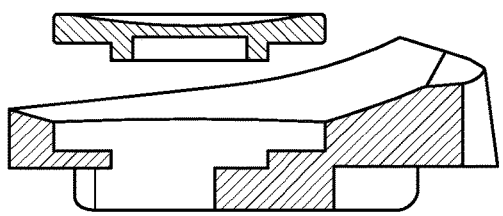
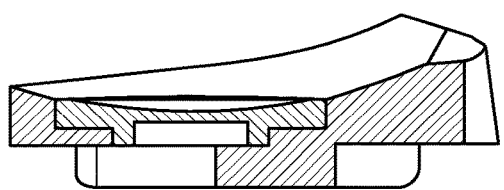
Figure 15D
Figure 15E

DEVICES AND METHODS TO PREVENT JOINT INSTABILITY FOLLOWING ARTHROPLASTY

CROSS-REFERENCE TO RELATED APPLICATION

This application is a national phase filing under 35 USC 371 of International Application No. PCT/US2017/046099, filed on Aug. 9, 2017, entitled "DEVICES AND METHODS TO PREVENT JOINT INSTABILITY FOLLOWING ARTHROPLASTY," which claims the benefit of commonly-owned U.S. Provisional Patent Application No. 62/372,487, filed Aug. 9, 2016, entitled "DEVICES AND METHODS TO TREAT JOINT INSTABILITY FOLLOWING ARTHROPLASTY," the contents of which are incorporated by reference herein in their entirety.

TECHNICAL FIELD

Various embodiments of the present invention relate to methods and systems to optimize the position and orientation of components in order to decrease the occurrence of joint instability after total joint arthroplasty. In particular, various embodiments of the present invention relate to methods and systems to optimize the position and orientation of components in order to decrease the occurrence of joint instability after total knee arthroplasty.

BACKGROUND

Using the knee as a non-limiting example, joint instability occurs when the soft-tissue structures around the knee are unable to provide the stability necessary for adequate function during standing or walking. Following arthroplasty, instability may be the result of increased soft-tissue laxity (looseness) due to improper positioning and/or alignment of the prosthesis. Pain and/or a sensation of the knee "giving way" may alter knee function and require revision surgery.

Joint instability is one of the major causes of revision after total knee arthroplasty (TKA). Aseptic loosening is one of the predominant mechanisms contributing to failure of TKA.

Classification of the tibiofemoral instability is based upon the direction of instability. The three basic types include coronal plane instability (collateral ligament instability, extension space instability), sagittal plane instability (anteroposterior instability, flexion space instability), and global instability.

Currently, techniques to increase joint stability are imprecise. For example, in TKA, "soft-tissue balancing"; which may involve releasing the medial or collateral ligaments to correct for a varus or valgus deformity and/or re-cutting aspect of the bone is an imprecise art. The amount of soft-tissue to be released to obtain a balanced knee is often uncertain. Similarly, the amount of bone to be re-cut in order to correct the balance of the knee is difficult to assess. In addition, the balance of the knee should be considered in combination with the overall alignment of the leg.

SUMMARY OF THE INVENTION

In one embodiment, the present invention provides a kit, comprising: (1) an alignment guide for preparing bone elements at a joint for receiving an implant; (2) a distractor comprising a member configured to engage with a first bone member, a member configured to engage with a second bone member, and a sensor, wherein the distractor is configured to move the first bone member away from the second bone member, wherein the sensor is configured to record (at the planning stage) at least one of (i) the force required to separate the first bone member from the second bone member; (ii) the orientation of the force required to separate the first bone member from the second bone member (iii) the pressure mapping resulting from the contact of one of the bone member against the sensor surface; (iv) the distance between the first and second bone members; and (v) the location of the contact of one of bone member against the sensor surface; (3) a plurality of trial members configured to receive at least one sensor; (4) at least one sensor configured to be integrated into an individual trial within the plurality and measure and report (at the verification stage) at least one of (i) the loading of the joint; (ii) the orientation of the load of the joint; (iii) the pressure mapping of the joint; and (iv) the location of the contact between one of the bone member on the sensor; and (5) an implant, optionally configured to receive the trial member assembled with at least one sensor and/or to articulate against the trial member assembled with at least one sensor.

In one embodiment, the present invention provides a kit, comprising: (1) an alignment guide for preparing the distal aspect of the femur and the proximal aspect of the tibia for receiving a femoral implant and a tibial implant; respectively; (2) a distractor comprising a tibial member engageable with the tibia and a femoral member engageable with the femur, and a sensor, wherein the distractor is configured to move the femur away from the tibia, wherein the sensor is configured to record (at the planning stage) at least one of (i) the force required to separate the femur from the tibia; (ii) the orientation of the force required to separate the femur from the tibia; (iii) the pressure mapping resulting from the contact of the femur against the sensor surface; (iv) the distance between the femur and tibia; and (v) the location of the contact of the femur against the sensor surface; (3) a plurality of tibial insert trials configured to be selected by a surgeon to assess the proper thickness of the final tibial insert component, wherein the tibial insert trials are further configured to receive at least one sensor; (4) at least one sensor configured to be integrated into an individual tibial insert trial within the plurality and measure and report (at the verification stage) at least one of (i) the loading of the tibiofemoral joint; (ii) the direction of the load; (iii) the pressure mapping of the tibiofemoral joint; and (iv) the location of the contact between preferably the femur on the sensor; (5) an implant, optionally configured to receive the tibial insert trial assembled with at least one sensor and/or to articulate against the tibial insert trial assembled with at least one sensor and (6) a computing device to display the at least one reported information wirelessly received from the at least one sensor.

In one embodiment, the at least one sensor has an elongated shape in the transversal plane; where its dimension along the antero-posterior axis is longer than its dimension along the medio-lateral axis.

In one embodiment, the distal aspect of the at least one sensor is configured to allow for assembly with the femoral paddle of the mechanical distractor as well as the plurality of tibial insert trials.

In one embodiment, the proximal aspect of the sensor-based device comprises a concave surface; wherein the curvatures are approximately similar to those of the proximal surface of an usual tibial insert trial of the same size.

In one embodiment, an individual tibial insert trial assembled with the at least one sensor has a similar proximal geometry as a usual tibial insert trial of the same size.

In one embodiment, the at least one sensor reports at least one parameter selected from the group consisting of: load value (available at planning and verification stages), load orientation (available at planning and verification stages), pressure mapping (available at planning and verification stages), joint gap (available at planning stage only) and contact location (available at planning and verification stages).

In one embodiment, the at least one parameter defines the location of the contact pattern between the native femur (at the planning stage) and/or or the femoral component (trial) (at the verification stage) against the at least one sensor.

In one embodiment, the at least one parameter is used, along with the displacement distance and/or displacement force, to define the stiffness of the soft tissue envelope of the joint.

In one embodiment, the at least one sensor reports the at least one parameter wirelessly to a computing device.

In an embodiment, a kit includes a distractor, a plurality of trial elements, and at least one sensor, the distractor configured to separate a first bone from a second bone adjacent to the first bone, the distractor having a first member and a second member configured to be positioned between the first bone and the second bone, a distance between the first member and the second member being adjustable to thereby separate the first bone from the second bone, the distractor further configured to receive at least one sensor in the first portion, each of the trial elements corresponding to a corresponding one of a plurality of surgical implants, each of the trial elements being configured to be temporarily coupled to the second bone so as to evaluate suitability of the corresponding one of the plurality of surgical implants for implantation, each of the trial elements further configured to receive at least one sensor, the at least one sensor configured to be selectively received in the distractor or one of the plurality of trial elements, wherein the at least one sensor is configured to record at least one of a magnitude of a force, a direction of application of a force, a pressure mapping, and/or a location of application of a force.

In an embodiment, the distractor is configured to receive two of the at least one sensor. In an embodiment, each of the plurality of trial elements is configured to receive two of the at least one sensor.

In an embodiment, the first bone is a femur and the second bone is a tibia. In an embodiment, the distractor is configured to receive a first one of the at least one sensor at a location corresponding to a medial condyle of the femur and to receive a second one of the at least one sensor at a location corresponding to a lateral condyle of the femur. In an embodiment, each of the plurality of trial elements is configured to receive a first one of the at least one sensor at a location corresponding to a medial condyle of the femur and to receive a second one of the at least one sensor at a location corresponding to a lateral condyle of the femur.

In an embodiment, each of the at least one sensor includes a variable sensor that is configured to provide a linear relationship between an applied force and an output voltage. In an embodiment, each of the at least one sensor is configured to wirelessly transmit data recorded by the each of the at least one sensor to a computing device. In an embodiment, the computing device is a computer-assisted orthopedic surgery system.

In an embodiment, the distractor is configured to record the distance between the first member and the second member. In an embodiment, each of the at least one sensor includes a Hall sensor and the second portion of the distractor includes a magnet, the Hall sensor and the magnet configured to cooperate to record the distance between the first member and the second member.

In an embodiment, the distance between the first member and the second member is adjustable in a range of between 5 mm and 19 mm. In an embodiment, the kit also includes a computer-assisted orthopedic surgery system. In an embodiment, the distractor includes a first recess configured to receive a first one of the at least one sensor and a second recess configured to receive a second one of the at least one sensor, each of the first and second recesses configured to receive the corresponding one of the first and second ones of the at least one sensor in a plurality of positions, whereby a distance between the first one of the at least one sensor and the second one of the at least one sensor can be adjusted.

In an embodiment, each of the at least one sensor has a proximal aspect that is contoured so as to resemble a native articular surface and a distal aspect that is configured to be selectively received in the distractor or one of the plurality of trial elements. In an embodiment, the distal aspect has a shape that is a one of a diamond, a square, a rectangle, an oblong shape, an ellipse, or an elongated freeform shape.

In an embodiment, a first one of the plurality of trial elements has a size that differs from a size of a second one of the plurality of trial elements. In an embodiment, the kit also includes a baseplate that is configured to be attached to the second bone. In an embodiment, each of the plurality of trial elements is configured to be removably received in the baseplate that is attached to the second bone.

BRIEF DESCRIPTION OF DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIG. 1 shows the elements of an exemplary kit.

FIG. 2A shows a side view representation of an exemplary mechanical distractor according to some embodiments of the present invention, the exemplary mechanical distractor being shown in a closed configuration.

FIG. 2B shows a side view representation of the exemplary mechanical distractor of FIG. 2A in an open configuration

FIG. 15A shows a top view and cross-sectional view of an exemplary embodiment of a tibial trial insert prior to receiving sensors therein.

FIG. 15B shows a top view and cross-sectional view of the tibial trial insert of FIG. 15A after receiving sensors therein.

FIG. 15C shows a top perspective view of an exemplary embodiment of a tibial trial insert and two exemplary sensors, prior to assembly of the sensors with the tibial trial insert.

FIG. 15D shows a cross-sectional view of the tibial trial insert and sensors of FIG. 15C.

FIG. 15E shows the cross-sectional view of FIG. 15D, after the sensors have been assembled with the tibial trial insert.

DESCRIPTION OF EXEMPLARY EMBODIMENTS

Figure 2C:
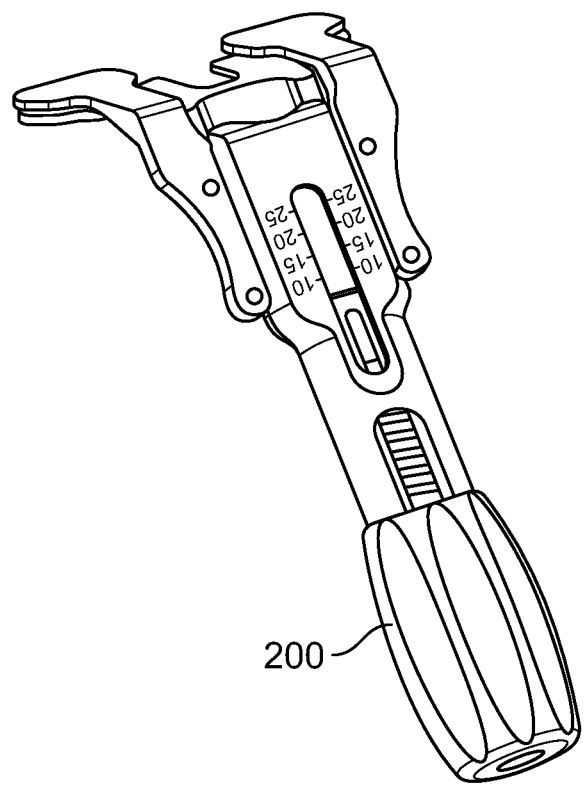
FIG. 2C shows a perspective view of the exemplary mechanical distractor of FIG. 2A.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, throughout the specification, the meaning of "a," "an," and "the" include plural references. The meaning of "in" includes "in" and "on."

Various embodiments of the present invention relate to methods and systems to optimize the position and orientation of components in order to decrease the occurrence of joint instability after total joint arthroplasty. In particular, various embodiments of the present invention relate to methods and systems to optimize the position and orientation of components in order to decrease the occurrence of joint instability after total knee arthroplasty.

Without intending to be limited to any particular theory, joint instability can be prevented by using a proper surgical technique that aims to balance the medial & lateral gaps in the implant joint (i.e., rectangular gaps) as well as the flexion & extension gaps in the implant joint.

Without intending to be limited to any particular theory, achieving a balanced knee joint and a proper alignment of the leg is expected to demonstrate proper ligament tension through the full range of motion, which provides a natural acting joint and minimizes pain and discomfort. Further, properly balanced ligaments reduce stress, wear and tear on the prosthesis and extend its life.

The present invention is directed to a method and kits intended to reduce the incidence of joint instability while maintaining a proper alignment of the joint. The method relates to the possibility of planning a bone cut based on both alignment and soft-tissue considerations (planning stage) and to then verify the achieved alignment and soft-tissue tension with the final or provisional implants in place (verification stage).

According to some embodiments, the same sensor device is used for both the planning stage and the verification stage.

In some embodiments, the present invention provides a kit, comprising: (1) an alignment guide for preparing the distal aspect of the femur and the proximal aspect of the tibia for receiving a femoral implant and a tibial implant; respectively; (2) a distractor comprising a tibial member engageable with the tibia and a femoral member engageable with the femur, and a sensor, wherein the distractor is configured to move the femur away from the tibia, wherein the sensor is configured to record (at the planning stage) at least one of (i) the force required to separate the femur from the tibia; (ii) the orientation of the force required to separate the femur from the tibia; (iii) the pressure mapping resulting from the contact of the femur against the sensor surface; (iv) the distance between the femur and tibia; and (v) the location of the contact of the femur against the sensor surface; (3) a plurality of tibial insert trials configured to be selected by a surgeon to assess the proper thickness of the final tibial insert component, wherein the tibial insert trials are further configured to receive at least one sensor; (4) at least one sensor configured to be integrated into an individual tibial insert trial within the plurality and measure and report (at the verification stage) at least one of (i) the loading of the tibiofemoral joint; (ii) the direction of the load; (iii) the pressure mapping of the tibiofemoral joint; and (iv) the location of the contact between preferably the femur on the sensor; (5) an implant, optionally configured to receive the tibial insert trial assembled with at least one sensor and/or to articulate against the tibial insert trial assembled with at least one sensor and (6) a computing device to display the at least one reported information wirelessly received from the at least one sensor.

Referring to FIG. 1, in some embodiments, a kit 100 includes a distractor 200, a set of tibial insert trials 300, and at least one sensor 400. The elements of the kit 100 will be discussed in detail hereinafter.

Figure 2D:
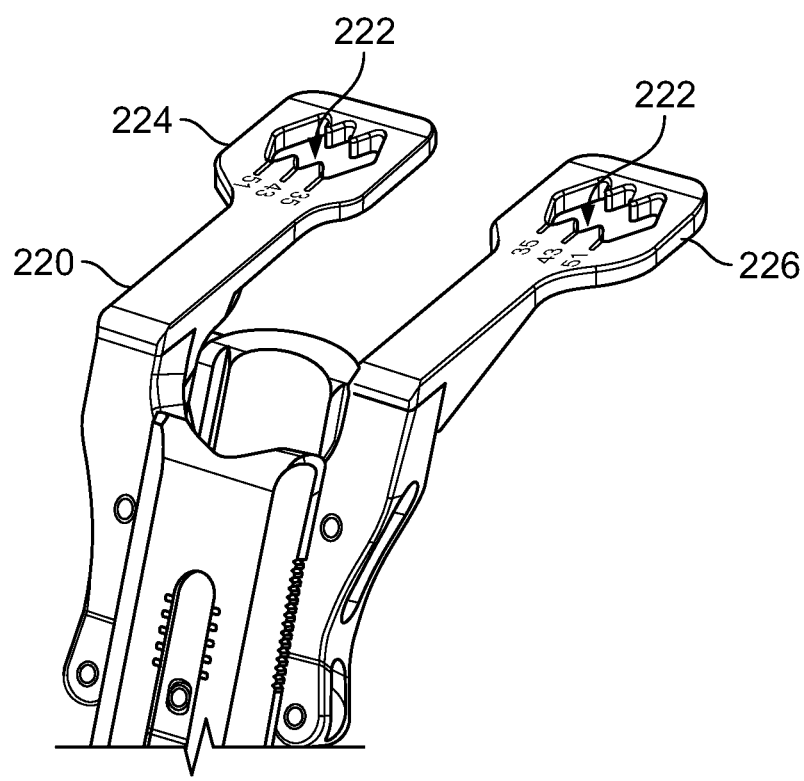
FIG. 2D shows a detailed view of a femoral paddle of the exemplary mechanical distractor of FIG. 2A.

Referring to FIGS. 2A-2D, an embodiment of a distractor 200 is shown. FIG. 2A shows a side view of the distractor 200 in a closed position, FIG. 2B shows a side view of the distractor 200 in an open position, FIG. 2C shows a perspective view of the distractor 200, and FIG. 2D shows a detailed view of a femoral member of the distractor 200. In some embodiments, the distractor 200 comprises a tibial member 210 engageable with the tibia and a femoral member 220 engageable with the femur. In some embodiments, the tibial member 210 includes a magnet. In some embodiments, a distraction mechanism is configured to move the femoral member 220 away from the tibial member 210 (and, thereby, move the femur away from the tibia) under a manually applied load, or, alternatively, through a force-applying mechanism. In some embodiments, the femoral member 220 features recesses 222 intended to receive sensors 400 according to some embodiments of the present invention. In some embodiments, the recesses 222 are diamond-shaped. In some embodiments, the femoral member 220 is configured to receive two of the sensors 400. In some embodiments, the femoral member 220 includes a first portion 224 having a recess 222 that is configured to receive a first one of the sensors 400 and a second portion 226 having a recess 222 that is configured to receive a second one of the sensors 400. In some embodiments, the first and second portions 224, 226 are configured such that, when the distractor 200 is in use, the recesses 222 are positioned along the mediolateral axis. In some embodiments, the femoral member 220 of the distractor 200 is configurable so as to adjust the mediolateral spread between the medial and the lateral sensors. In some embodiments, the spread between the medial sensor and the lateral sensor is adjustable so that the spread can be similar to the distance between the lowest aspects of the medial and lateral condyles of the native femur. FIG. 2D shows a detailed view of the femoral member 220. In the embodiment shown in FIG. 2D, each of the first and second portions 224, 226 of the femoral member 220 includes a plurality of the recesses 222, each of which is configured to receive one of the sensors 400. In some embodiments, each of the first and second portions 224, 226 of the femoral member 220 includes an overlapping plurality of the recesses 222, each of which is configured to receive one of the sensors 400. In some embodiments, by placing a first sensor 400 in a selected one of the recesses 222 in the first portion 224 of the femoral member 220, and by placing a second sensor 400 in a selected one of the recesses 222 in the second portion 226 of the femoral member 220, the distance between the sensors 400 (e.g., in a mediolateral direction) may be adjusted so as to be similar to the distance between the lowest aspects of the medial and lateral condyles of the native femur.

Figure 3:
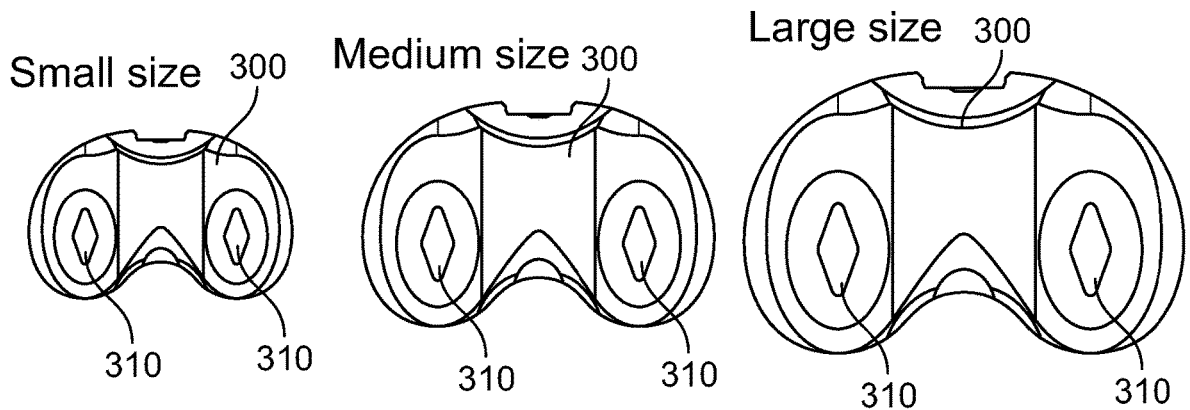
FIG. 3 shows individual tibial trials in a plurality of tibial trials according to some embodiments of the present invention.

Referring to FIG. 3, in some embodiments, the kit 100 includes a set of tibial insert trials 300 that are configured for use to assess the proper thickness of the final tibial insert component. FIG. 3 illustrates a set of tibial insert trials 300 that includes the tibial insert trials 300 in at least three (3) different sizes (e.g., small, medium, and large), but it will be apparent to those of skill in the art that this is only exemplary and that any number of different sizes may be included in other exemplary sets. In some embodiments, the tibial trials 300 include recesses 310 at the level of each condylar dish of the tibial trials 300, the recesses 310 being configured to receive one of the sensors 400. In some embodiments, the recesses 310 are diamond-shaped.

In one embodiment, the tibial trials 300 are similar to those described in U.S. Patent Application Publication No. 2003/0069644A1 other than as described herein. In one embodiment, the tibial trials 300 are similar to those described in U.S. Pat. No. 7,097,662 other than as described herein. In some embodiments, an individual one of the tibial trials 300 that has been provided with one of the sensors 400 has a similar proximal geometry to that of a usual tibial insert trial (i.e., a tibial insert trial lacking a sensor) of the same size.

Figure 4A:
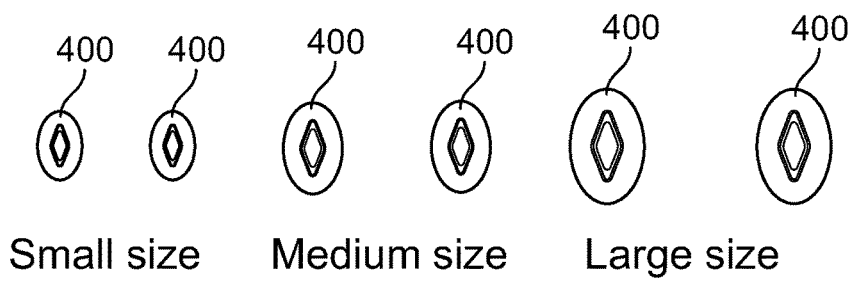
FIG. 4A shows side views of various sensors according to some embodiments of the present invention.
Figure 4B:
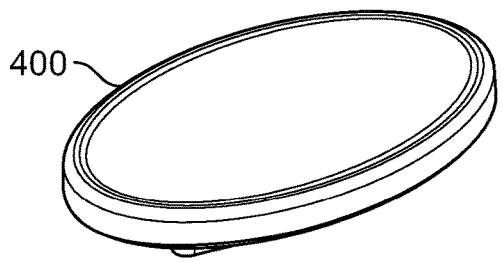
FIG. 4B shows a top perspective view of an exemplary embodiment of a sensor.
Figure 4C:
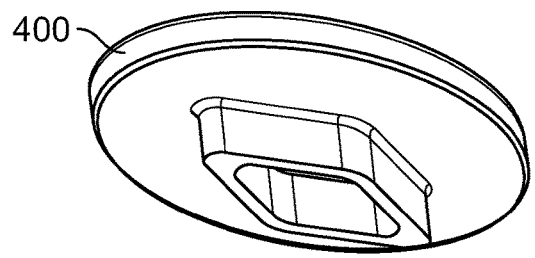
FIG. 4C shows a bottom perspective view of the sensor of FIG. 7A.

Referring to FIGS. 4A and 4B, in some embodiments, the kit 100 includes at least one sensor 400. FIG. 4A shows side views of sensors 400 from a kit 100 that includes sensors 400 in at least three (3) different sizes (e.g., small, medium, and large), but it will be apparent to those of skill in the art that this is only exemplary, and that other embodiments of a kit 100 may include sensors of a single size or sensors of any other number of sizes. FIGS. 4B and 4C show top and bottom perspective views, respectively, of an exemplary sensor 400. In some embodiments, the kit 100 includes two (2) of the sensors 400 in a single size. In some embodiments, the kit 100 includes two (2) of the sensors 400 in each of a plurality of sizes. In some embodiments, the sensors 400 are configured to be received in the recesses 222 of the distractor 200 and in the recesses 310 of the tibial trials 300. In some embodiments, the at least one sensor 400 has a distal aspect 410 that is configured to allow for assembly selectively with either the femoral member 220 of the distractor 200 or with one of the plurality of tibial insert trials 300. In some embodiments, the distal aspect 410 is diamond-shaped. In some embodiments, the distal aspect 410 has a different shape (and, correspondingly, the recesses 222 of the distractor 200 and the recesses 310 of the tibial trials 300 have a different shape as well). In some embodiments, the distal aspect 410 has a shape that is configured to prevent rotation of the sensor 400 with respect to the distractor 200 and to the tibial trials 300. In some embodiments, the distal aspect 410 has a shape that is either a square, a rectangle, an oblong shape, an ellipse, or an elongated freeform shape. In some embodiments, the at least one sensor 400 has a proximal aspect 420 that is shaped concavely such that, when the at least one sensor 400 is assembled to one of the plurality of tibial insert trials 300, the resulting curvature is approximately similar to the curvature of the proximal aspect of a usual tibial insert trial (e.g., a tibial insert trial that lacks a sensor) of the same size.

In some embodiments, the at least one sensor 400 is similar to that described in U.S. Patent Application Publication No. 2007/0233267 A1 other than as described herein. In some embodiments, the at least one sensor 400 is similar to that described in U.S. Pat. No. 7,587,945 other than as described herein. In some embodiments, the at least one sensor 400 is similar to that described in U.S. Pat. No. 7,097,662 other than as described herein. In some embodiments, the at least one sensor 400 includes a Hall sensor.

In some embodiments, the at least one sensor 400 includes a variable resistor which is set up in an amplification circuit to create a linear relationship between load input and voltage output or any other known technology able to record at least one parameter. In some embodiments, the at least one sensor 400 includes an array of force sensitive aspects. In some embodiments, a force is recorded at each position within the array by interpreting a change in impedance (e.g. resistive, capacitive, or inductive), or deformation (e.g., piezoelectric, magneto-elastic, optical, or change in resonance). In some embodiments, the data output by the sensor 4000 is interpreted by a processing module, which calculates a data array consisting of forces and/or spatial data.

In some embodiments, the at least one sensor 400 includes a piezoelectric sensor configured such that, when a load is applied to the sensor, an electrostatic charge proportional to the load is generated. In some embodiments, the at least one sensor 400 includes a strain gauge configured such that, when the strain gauge deforms in response to deformation (i.e., in response to a load), a change in electrical resistance results. In some embodiments, the at least one sensor 400 includes a plurality of layers. In some embodiments, the at least one sensor 400 includes three or more layers. In some embodiments, the resistance of an inner layer (e.g., of a sensor 400 including a plurality of layers) changes proportionally in response to deformation (i.e., in response to a load). In some embodiments, the capacitance between two layers (e.g., of a sensor 400 including a plurality of layers) changes proportionally in response to deformation (i.e., in response to a load).

In some embodiments, the at least one sensor 400 is configured to record at least one of (i) a force (e.g., when the at least one sensor is received in the distractor 200, the force required to separate the femur from the tibia); (ii) an orientation of a force (e.g., when the at least one sensor is received in the distractor 200, the orientation of the force required to separate the femur from the tibia); (iii) a pressure mapping resulting from a force (e.g., when the at least one sensor is received in the distractor 200, the pressure mapping resulting from the contact of the femur against the sensor surface); and (iv) a location of contact (e.g., when the at least one sensor is received in the distractor 200, the location of the contact of the femur against the sensor surface). In some embodiments, the at least one sensor 400 is configured to wirelessly transmit sensed data to an external device (e.g., a CAOS system, as will be described hereinafter).

In some embodiments, the at least one sensor 400 has an elongated shape in the transversal plane; that is, when the at least one sensor 400 is received in either the distractor 200 or one of the tibial insert trials 300, and the distractor 200 or the one of the tibial insert trials 300 is positioned in its normal manner with respect to a patient's body, the dimension of the at least one sensor 400 along the antero-posterior axis is longer than the dimension of the at least one sensor 400 along the medio-lateral axis.

Figure 5:
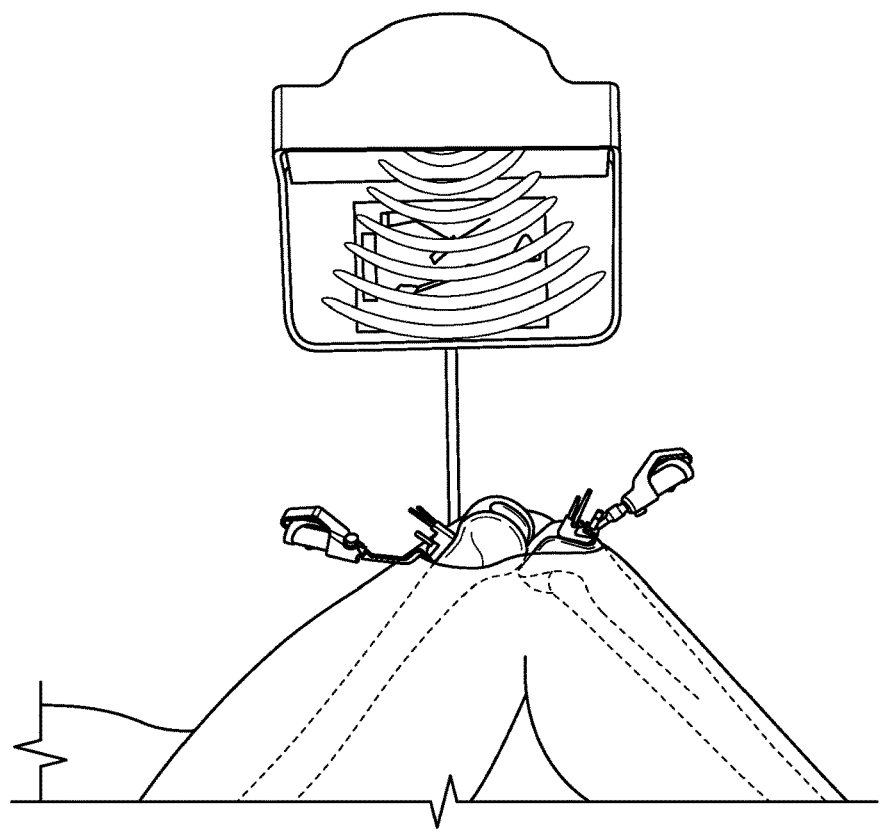
FIG. 5 shows a representation of a computer-assisted orthopedic surgery system to aid a surgeon to place components of a joint implant in connection with some embodiments of the present invention.

Referring to FIG. 5, in some embodiments, the kit 100 is used in connection with an alignment guide for preparing bone elements at a joint for receiving an implant. In some embodiments, the alignment guide includes a conventional mechanical instrumentation. In some embodiments, the alignment guide includes a computer-assisted orthopedic surgery (CAOS) system. In some embodiments, CAOS systems are configured to assist surgeons in placing the knee components relative to the acquired patient's anatomical landmarks. In some embodiments, a CAOS system includes a computer, a display unit, and a tracking system. In some embodiments, the CAOS system is similar to that disclosed in U.S. Pat. No. 8,403,934.

Figure 6:
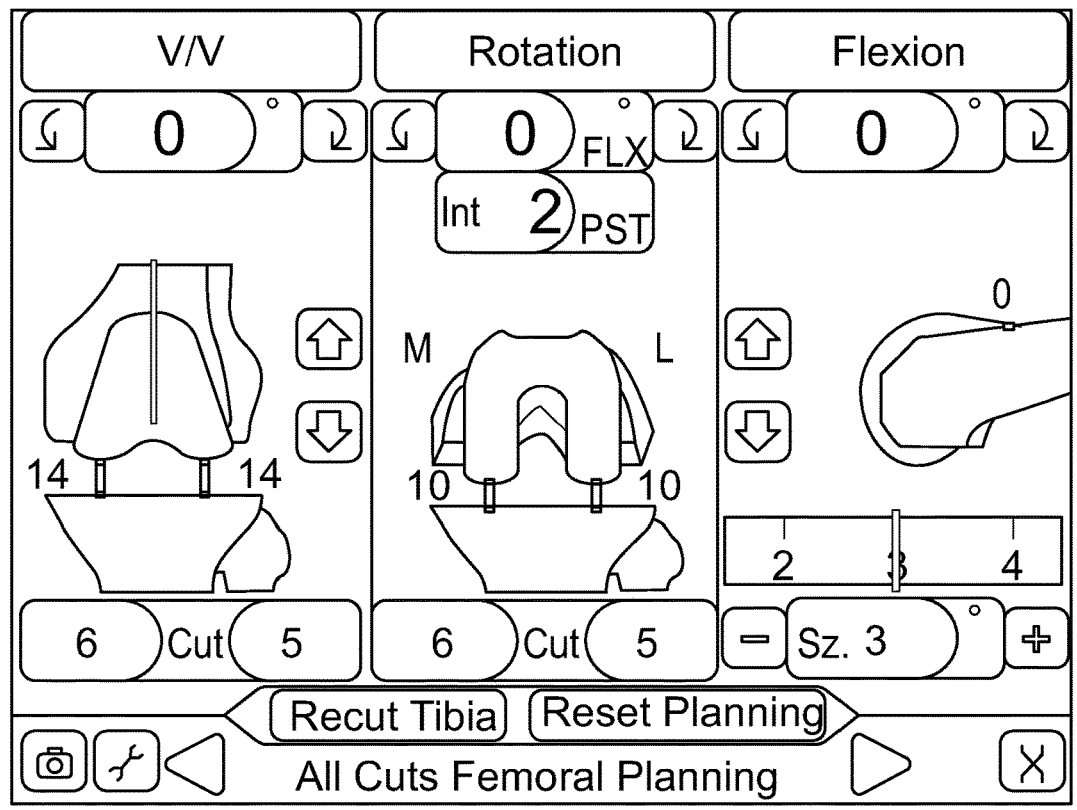
FIG. 6 shows an exemplary screenshot taken during use of the computer assisted orthopedic surgery system of FIG. 5 according to some embodiments of the present invention.

CAOS systems are widely recognized as an effective tool to provide surgeons with guidance in terms of accuracy and precision of knee implant alignment. They allow surgeons to plan for the tibial and femoral resection parameters based on their preference relative to the acquired anatomical landmarks. This ensures proper alignment of the components relative to the mechanical axis. FIG. 6 shows an graphical user interface that may be generated by a CAOS system to this end. While achieving proper alignment is of paramount importance, it does not ensure proper balance of the soft-tissue envelope over the range of flexion. In other words, the knee joint may be perfectly aligned relative to the mechanical axis but still presents some instability over the range of flexion.

In some embodiments, the CAOS system is configured to wirelessly receive data from the at least one sensor 400, to treat the data, and to display the data to the surgeon. In some embodiments, a different type of monitoring device is configured to wirelessly receive data from the at least one sensor 400, to treat the data, and to display the data to the surgeon.

In some embodiments, the distractor 200 is configured to record (at the planning stage) the displacement of the femoral member 220 relative to the tibial member 210 during the distraction of the knee joint by tracking the position of the at least one sensor 400 attached to the femoral member 220 of the distractor relative to the tibial member 210 of the distractor 200 placed against the proximal tibial cut and wirelessly transmit the information (i.e., displacement) to a computing device. In some embodiments, the computing device is a CAOS system. In some embodiments, the computing device is another type of device (e.g., computer, tablet, smartphone, . . . ) able to wirelessly receive data from the sensor 400. Regardless the nature of the computing device, it is configured to treat the data and then display them to the surgeon.

In some embodiments, the displacement is evaluated by a Hall sensor encapsulated inside the sensor 400 attached to the femoral member 220 of the distractor 200 relative to a magnet attached to the tibial member 210 of the distractor 200. In some embodiments, the displacement can also be directly measured by the CAOS system by tracking the motion of the tracker attached to the femur relative to the tracker attached to the tibia. In some embodiments, the displacement is evaluated by another known technique for determining a displacement between two objects.

In some embodiments, the at least one sensor is used in multiple applications during a surgical procedure. For example, in some embodiments, the at least one sensor is configured to record at least one of (i) the force required to separate the femur from the tibia; (ii) the orientation of the force required to separate the femur from the tibia; (iii) the pressure mapping resulting from the contact of the femur against the sensor surface; (iv) the distance between the femur and tibia; and (v) the location of the contact of the femur against the sensor surface. In some embodiments, the at least one sensor is configured to be attached to a joint tensing apparatus (at the planning stage, before the preparation of the femoral cuts), or to be attached to trial implants (at the verification stage, after the preparation of the femoral cuts) so as to assess intraoperative loads, or to be attached to the selected prosthetic insert to allow load sensing post operatively. In some embodiments, the proximal aspect of the sensor is configured to contact the native femur (at the planning stage) or the femoral component (at the verification stage). In some embodiments, the proximal aspect of the sensor is flat. In some embodiments, the proximal aspect of the sensor has a geometry that matches the articulation being evaluated. While the knee is shown as the preferred embodiment, and may include the femoral-tibial articulation(s) and the patella articulation, the at least one sensor, and the kits described herein have application in other joints, including but not limited to the shoulder, ankle, wrist and other articulating joints of the body.

Consequently, in some embodiments, the present invention provides a kit, comprising: (1) an alignment guide for preparing bone elements at a joint for receiving an implant; (2) a distractor comprising a member configured to engage with a first bone member, a member configured to engage with a second bone member, and a sensor, wherein the distractor is configured to move the first bone member away from the second bone member, wherein the sensor is configured to record (at the planning stage) at least one of (i) the force required to separate the first bone member from the second bone member; (ii) the orientation of the force required to separate the first bone member from the second bone member (iii) the pressure mapping resulting from the contact of one of the bone member against the sensor surface; (iv) the distance between the first and second bone members; and (v) the location of the contact of one of bone member against the sensor surface; (3) a plurality of trial members configured to receive at least one sensor; (4) at least one sensor configured to be integrated into an individual trial within the plurality and record (at the verification stage) at least one of (i) the loading of the joint; (ii) the orientation of the load of the joint; (iii) the pressure mapping of the joint; and (iv) the location of the contact between one of the bone member on the sensor; and (5) an implant. In some embodiments, the implant is configured to receive the trial member assembled with at least one sensor and/or to articulate against the trial member assembled with at least one sensor.

In some embodiments, the at least one sensor is configured to record at least one parameter selected from the group consisting of: load value, load orientation, pressure mapping, and contact location. In some embodiments, the at least one parameter defines the location of the contact pattern between the native femur (at the planning stage) and/or the femoral trial component (at the verification stage) against the at least one sensor.

In some embodiments, the at least one parameter is used, along with the displacement distance and/or displacement force, to define the stiffness of the soft tissue envelope of the joint. In some embodiments, the at least one sensor reports the at least one parameter wirelessly.

In some embodiments, the distractor 200 provides overall guidance regarding the soft-tissue in extension and/or flexion and/or at any degree of flexion of the knee. Distractors include, for example, simple laminar spreaders to complex tensors able to quantify the joint gap(s) as well as the load. However, distractors are typically used in extension and/or in flexion, so the status of the soft-tissue envelope between these two discrete and pre-defined angles of flexion or above 90° of flexion is unknown. While achieving balanced and equal gaps in extension and/or at 90° of flexion is a desired outcome, a substantial amount of cases are associated with instability occurring between 30° and 60° of flexion (aka. mid flexion instability); which is a range of flexion angles not tested by usual distractors. Further, when using such instrument, the knee joint balancing is performed under a distraction load usually ranging from 20 lbs. to 60 lbs. Unfortunately, there is no consensus regarding the optimum load to be used. Because of the absence of consensus regarding the inputs (i.e., the distraction load), the output (i.e., joint gap) is questionable.

In some embodiments, the mechanical distractor 200 further comprises at least one additional sensor beyond the sensor 400. In some embodiments, the additional sensor included in the mechanical distractor 200 is the sensor is the sensor described in U.S. Pat. No. 4,066,082. In some embodiments, each tibial insert trial 300 further comprises at least one additional sensor beyond the sensor 400. In some embodiments, the additional sensor included in each tibial insert trial 300 is the sensor described in U.S. Patent Application Publication No. 2007/0233267 A1.

Figure 7:
FIG. 7 shows the main dimensions of the native femur to be used for the selection of the sensor and their position on the distractor.

In some embodiments, an exemplary system (e.g., a system including the kit 100) is employed in a surgical method, such as the method described below. For the purpose of this proposed description, the alignment guide for preparing the proximal tibia and distal femur for receiving an implant comprises a computer-assisted orthopedic surgery (CAOS) system. In some embodiments, at the beginning of the procedure, the CAOS system is initiated. Next, in some embodiments, the surgeon exposes the knee joint according to his/her preferred surgical technique and attaches tibial and femoral trackers to the tibia and femur, respectively. In some embodiments, once the trackers have been attached to the bones, the surgeon performs the acquisitions of the femoral and tibial anatomical landmarks using a navigated probe. In some embodiments, based on the computation of the acquisitions, the CAOS system provides information in term of leg alignment, anteroposterior size of the distal extremity of the native femur (e.g., measurement A shown in FIG. 7), and spread between the condyles (e.g., measurement B shown in FIG. 7).

In some embodiments, from the kit 100 including at least one of the sensors 400 (e.g., from a kit that includes small, medium, and large sensors as shown in FIG. 4A), the surgeon selects the sensors 400 that approximately matches the computed femoral size (e.g., measurement A shown in FIG. 7) and connects the selected sensors 400 with the computing device of the CAOS system using a wireless type of communication.

Figure 8A:
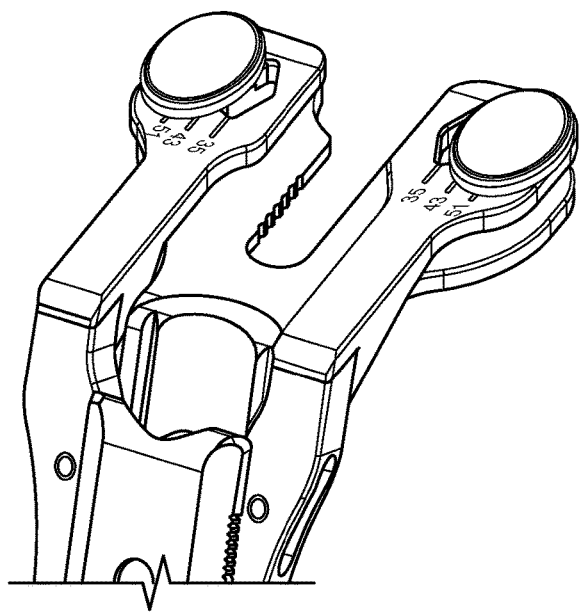
FIG. 8A shows a femoral paddle of an exemplary distractor with exemplary sensors positioned in a in a wide position.
Figure 8B:
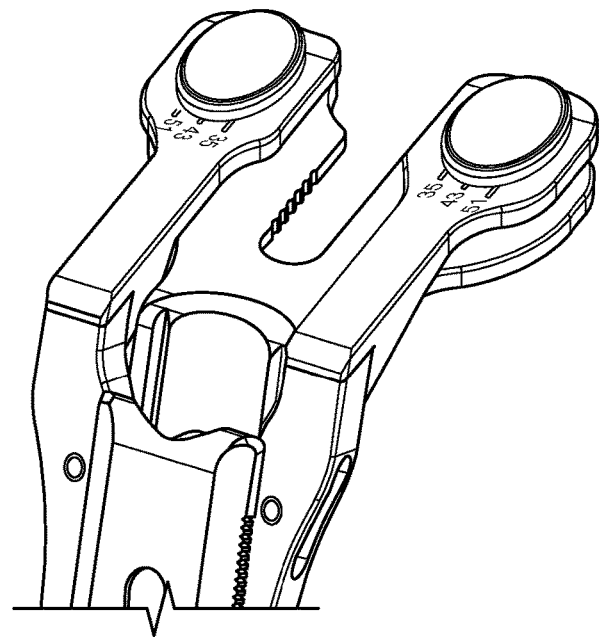
FIG. 8B shows the femoral paddle of FIG. 8A with the exemplary sensors positioned in a in a central position.
Figure 8C:
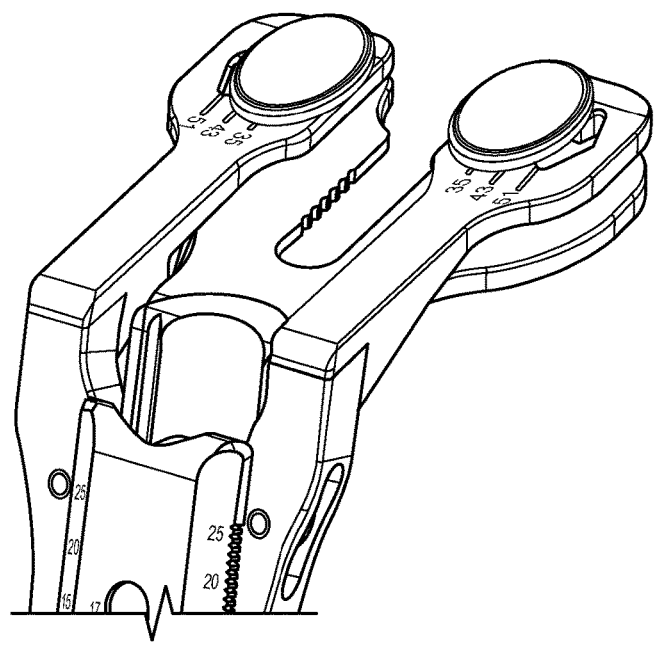
FIG. 8C shows the femoral paddle of FIG. 8A with the exemplary sensors positioned in a in a narrow position.

In some embodiments, based on the knowledge of the spread between the condyles of the native femur (i.e., measurement B shown in FIG. 7), the surgeon assembles the selected sensors 400 with femoral member 220 of the distractor 200 by placing the sensors 400 at the proper mediolateral spread (e.g., in ones of the recesses 222 selected so as to provide the proper mediolateral spread). FIG. 8A shows the femoral member 220 of the distractor 200 with sensors 400 positioned in the most lateral ones of the recesses 222. FIG. 8B shows the femoral member 220 of the distractor 200 with sensors 400 positioned in centrally positioned ones of the recesses 222. FIG. 8C shows the femoral member 220 of the distractor 200 with sensors 400 positioned in the most medial ones of the recesses 222. In some embodiments, as a result, the distance between the lowest point of the proximal articular surface of the selected ones of the sensors 400 is similar to the spread between the two condyles of the native femur (e.g., measurement B shown in FIG. 7); which is helpful for the planning stage. Similarly, in some embodiments, the size of the selected one of the tibial insert trials 300 (e.g., small, medium, large, etc.) matches the size of the femoral component, and, as a result, the size of the sensor 400 (e.g., small, medium, large, etc.) is the same as the size as the femoral component (i.e., size A), which is helpful during the verification stage.

Figure 9:
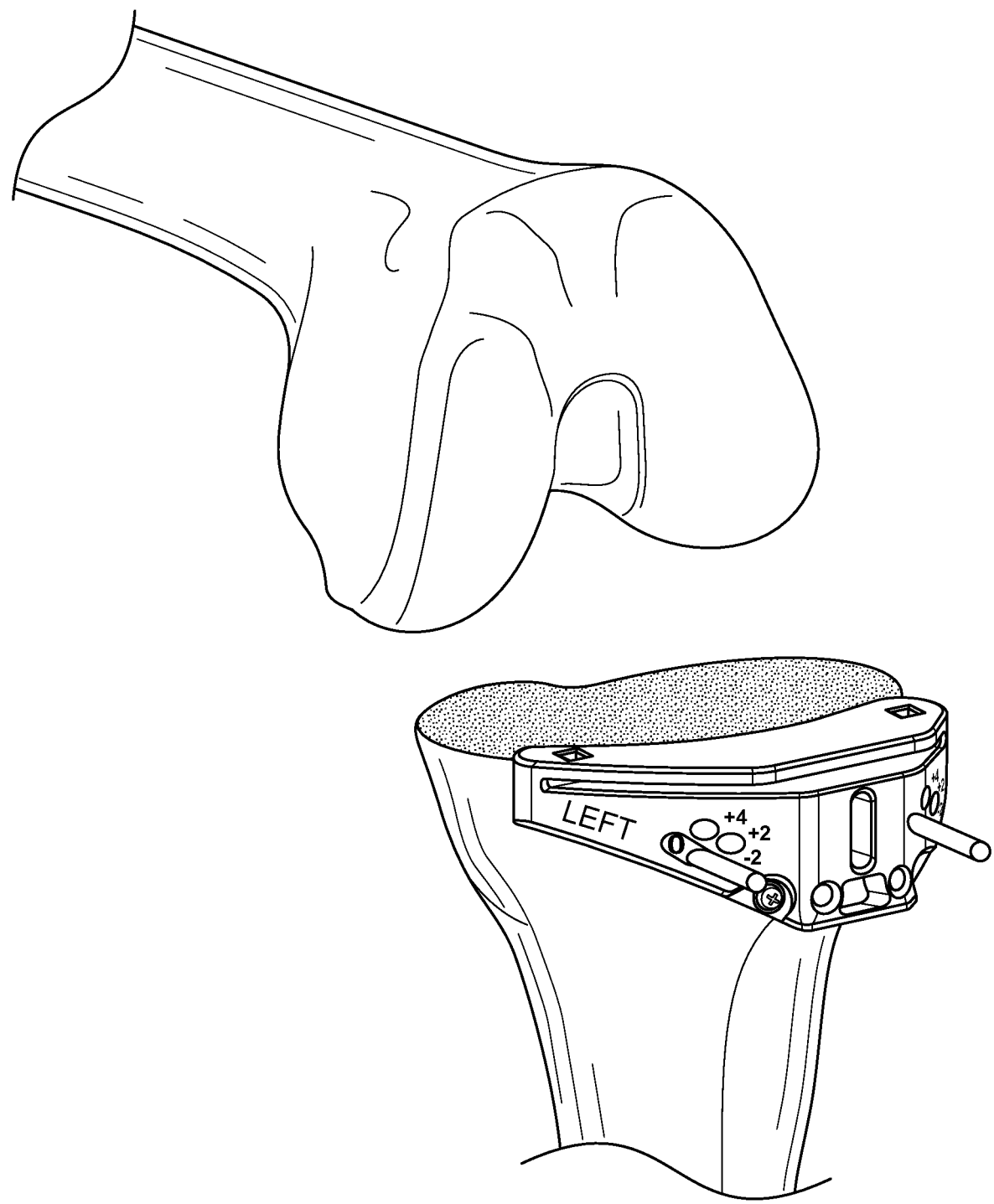
FIG. 9 shows a femur and tibia of a knee joint after the tibia has been prepared.
Figure 10:
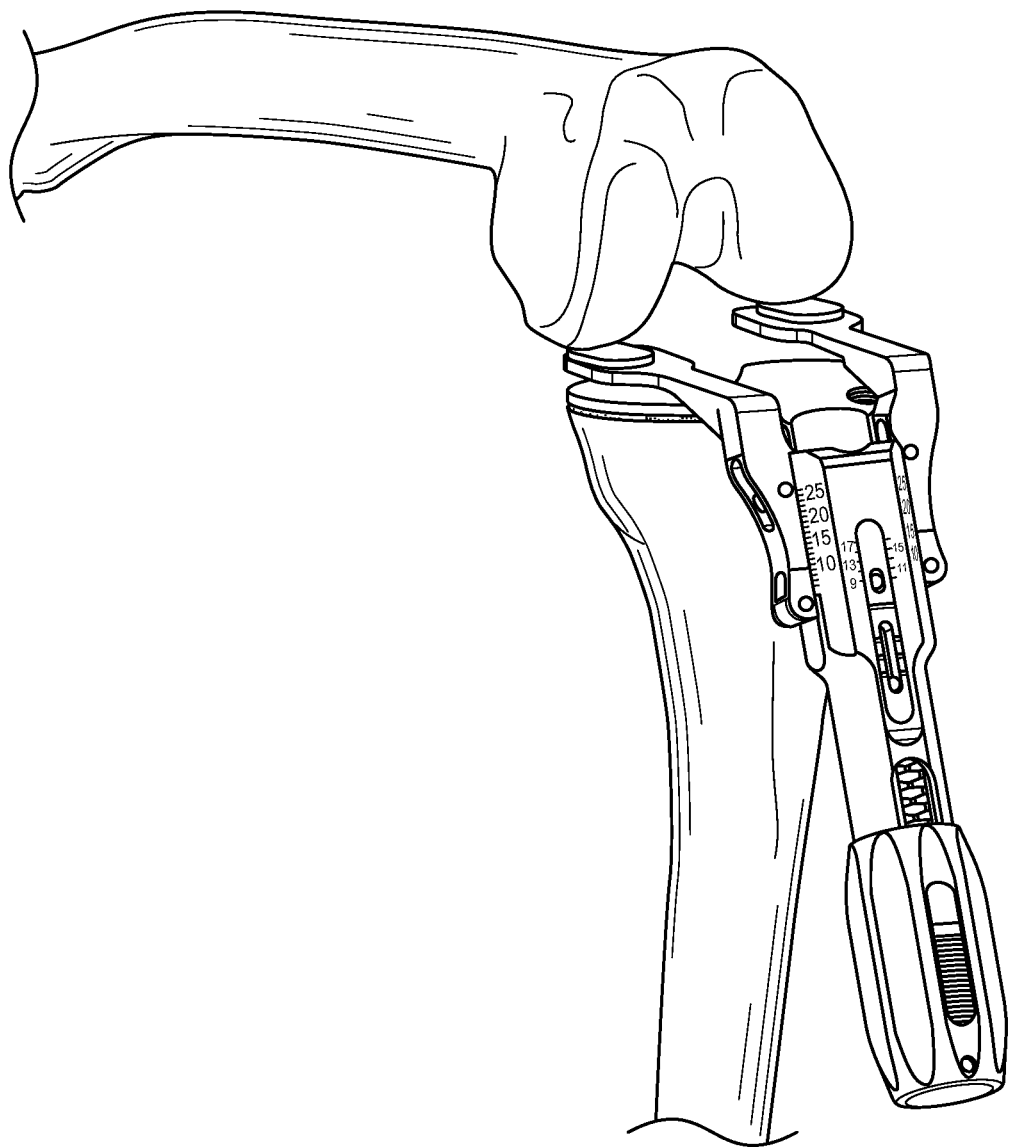
FIG. 10 shows the exemplary distractor of FIG. 2A as positioned in the knee joint after the tibia has been prepared.

In some embodiments, the surgeon performs the proximal tibial cut (or a preliminary proximal tibial cut) using the guidance from the CAOS system. In some embodiments, the tibial cut is at least 5 mm thick. FIG. 9 shows a femur and tibia after the proximal tibial cut has been made. In some embodiments, once the proximal tibial cut has been checked and confirmed to be in accordance with the plan from the CAOS system, then the surgeon inserts the assembled distractor 200 (i.e., the distractor 200 with the selected sensors 400 in place) between the proximal tibial cut and the native femur. FIG. 10 shows the distractor 200 as positioned in this manner. As noted above with reference to FIG. 2, the anticipated opening distance of the distractor 200, which is measured as the minimum distance between the distal aspect of the tibial member to the lowest point of the concave surface of the sensors 400 may typically range from 5 mm (i.e., the size of the distractor 200 when in its closed configuration) to 19 mm (i.e., the size of the distractor 200 when in its open configuration).

Figure 11:
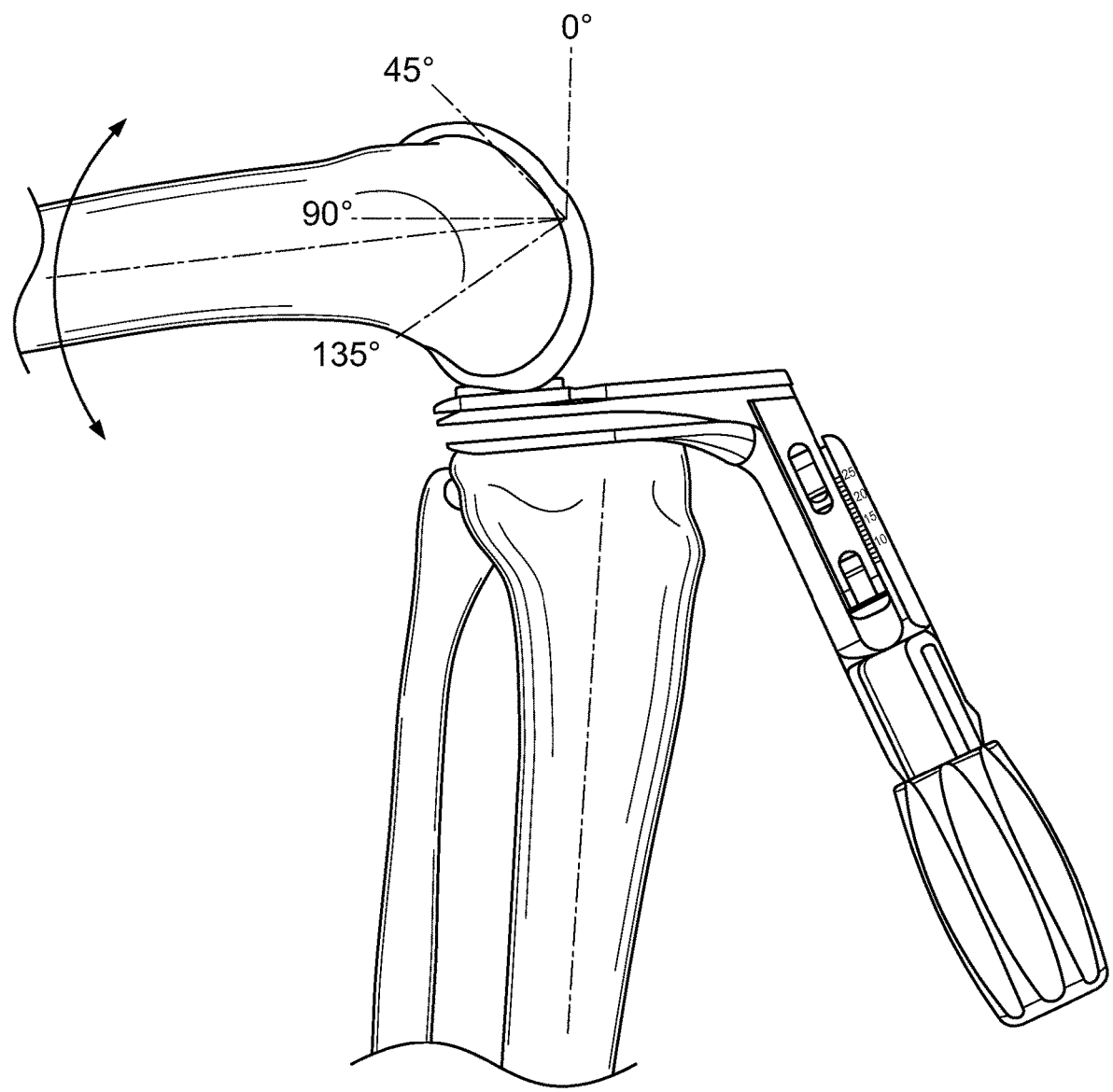
FIG. 11 shows various flexion angles of the knee while the exemplary distractor is positioned as in FIG. 10.
Figure 12:
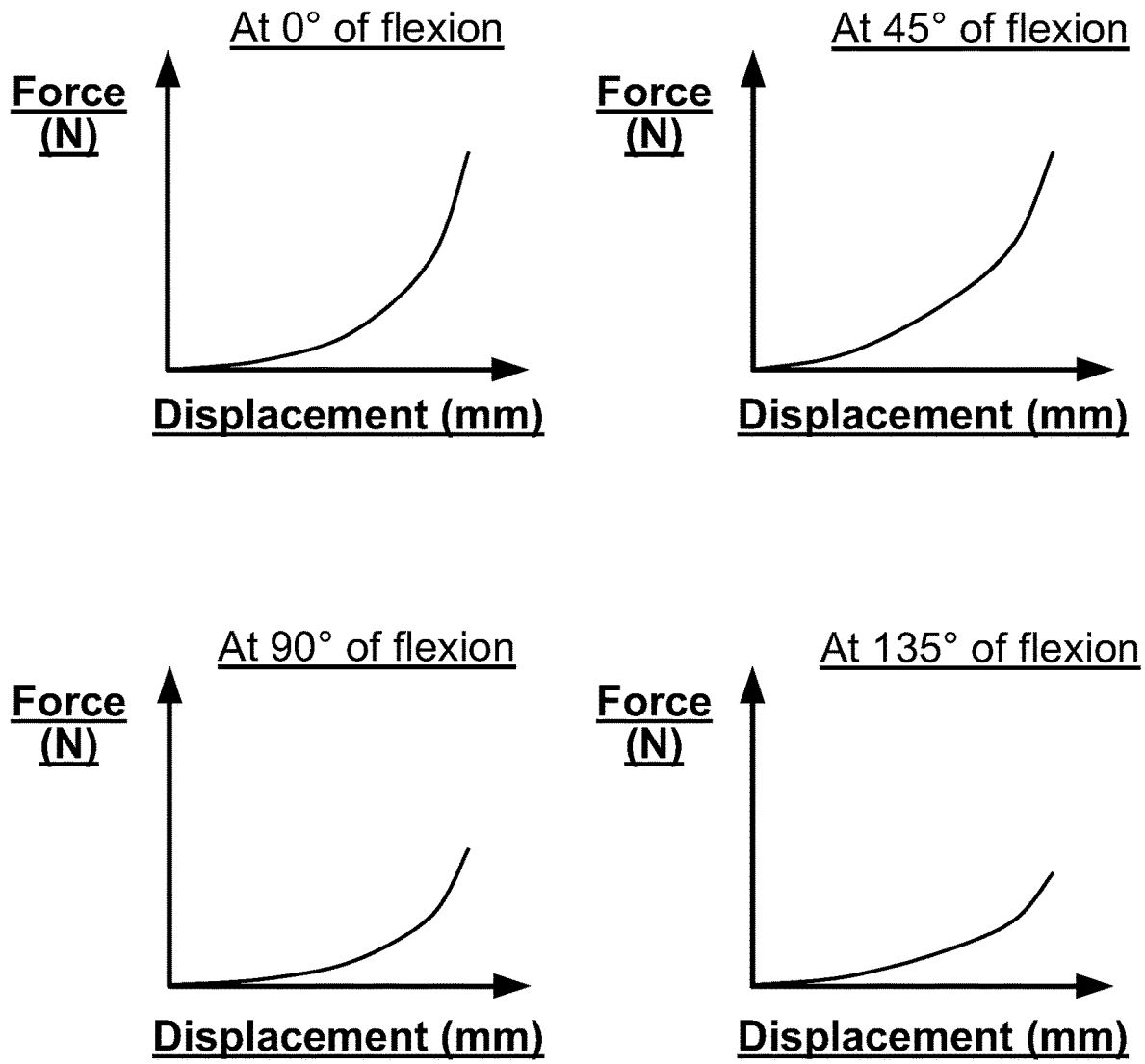
FIG. 12 shows data that may be recorded by the exemplary sensor while installed in the exemplary distractor as positioned in FIG. 10.

In some embodiments, at this point, the surgeon places the leg at different angles of flexion, preferably ranging from extension (i.e., 0° of flexion) to the full passive flexion allowed by the patient (e.g., 140° of flexion). In some embodiments, the leg is moved at various angular increments depending on the number of acquisition points desired by the surgeon. In some embodiments, the angular increments are in the range between 10° and 45° depending of the number of acquisition points requested by the surgeon. FIG. 11 shows the leg during this process, positioned at approximately 105° of flexion. In some embodiments, at each degree of flexion measured by the CAOS system, the surgeon manually actuates the distractor 200 to separate the femoral member 220 from the tibial member 210. In some embodiments, because the tibial member 210 contacts the proximal tibial cut and the sensors 400 attached to the femoral member 220 contact the native femur, such separation of the femoral member 220 from the tibial member 210 results into a separation of the native femur from the proximal tibial cut. In some embodiments, during the distraction, the sensors 400 record at least one of (i) the force required to separate the femur from the tibia; (ii) the orientation of the force required to separate the femur from the tibia; (iii) the pressure mapping resulting from the contact of the femur against the surface of the sensors 400; (iv) the distance between the femur and tibia; and (v) the location of the contact of the femur against the surface of the sensors 400. In some embodiments, the surgeon configures the sensors 400 (e.g., via the CAOS system) to recorded a selected one or more of the parameters noted above. In some embodiments, the recorded information is wirelessly transmitted to the CAOS system so it can be displayed to the surgeon. FIG. 12 shows data recorded by the at least one sensor 400 as configured to record force, at four different flexion angles.

In some embodiments, based on the acquisition of the recorded information, the CAOS system may provide a feedback loop. For example, in some embodiments, the CAOS system is configured alert the surgeon or stop the distraction when the recorded load is above a threshold (e.g., 300 N) previously defined by the surgeon. In some embodiments, the CAOS system is configured to alert the surgeon or stop the distraction when the recorded stiffness (e.g., ratio of load to displacement) is above a threshold previously defined by the surgeon. In some embodiments, the CAOS system is configured to alert the surgeon or stop the distraction when the recorded displacement (or distraction) is above a threshold (e.g., 19 mm) previously defined by the surgeon. In some embodiments, such alerts are intended to ensure that the acquisition process does not damage the soft-tissue envelope.

In some embodiments, based on the load/displacement curves obtained at discrete angles of flexion and the alignment data from the CAOS system (e.g., the curves shown in FIG. 12), the surgeon plans the position and orientation of the femoral component relative to the native femur. This use of the sensors 400 and the data recorded thereby is referred to herein as the "planning stage". In some embodiments, the planned target is based on information from both the CAOS system (e.g., the alignment and sizing of the components) and the sensors (e.g., the data recorded by the sensors, which may be referred to as the "soft-tissue signature") in order to achieve both a mechanically aligned and balanced knee. In some embodiments, the definition of the proper soft-tissue tension to be used for the plan is a parameter up to the choice of the surgeon. Generally, the surgeon leverages the load/displacement curves in order to define the joint gap (i.e., the distance between the femur and the tibia) under a defined load. In some embodiments, from the knowledge of these gaps, the surgeon is able to leverage the CAOS system in order to position and orient the femoral component. In some embodiments, the surgeon selects the femoral component based on the change of slope of the load-displacement curve in order to define the optimal tension of the soft-tissue envelope, as described in European Patent No. EP 1304093.

Figure 13:
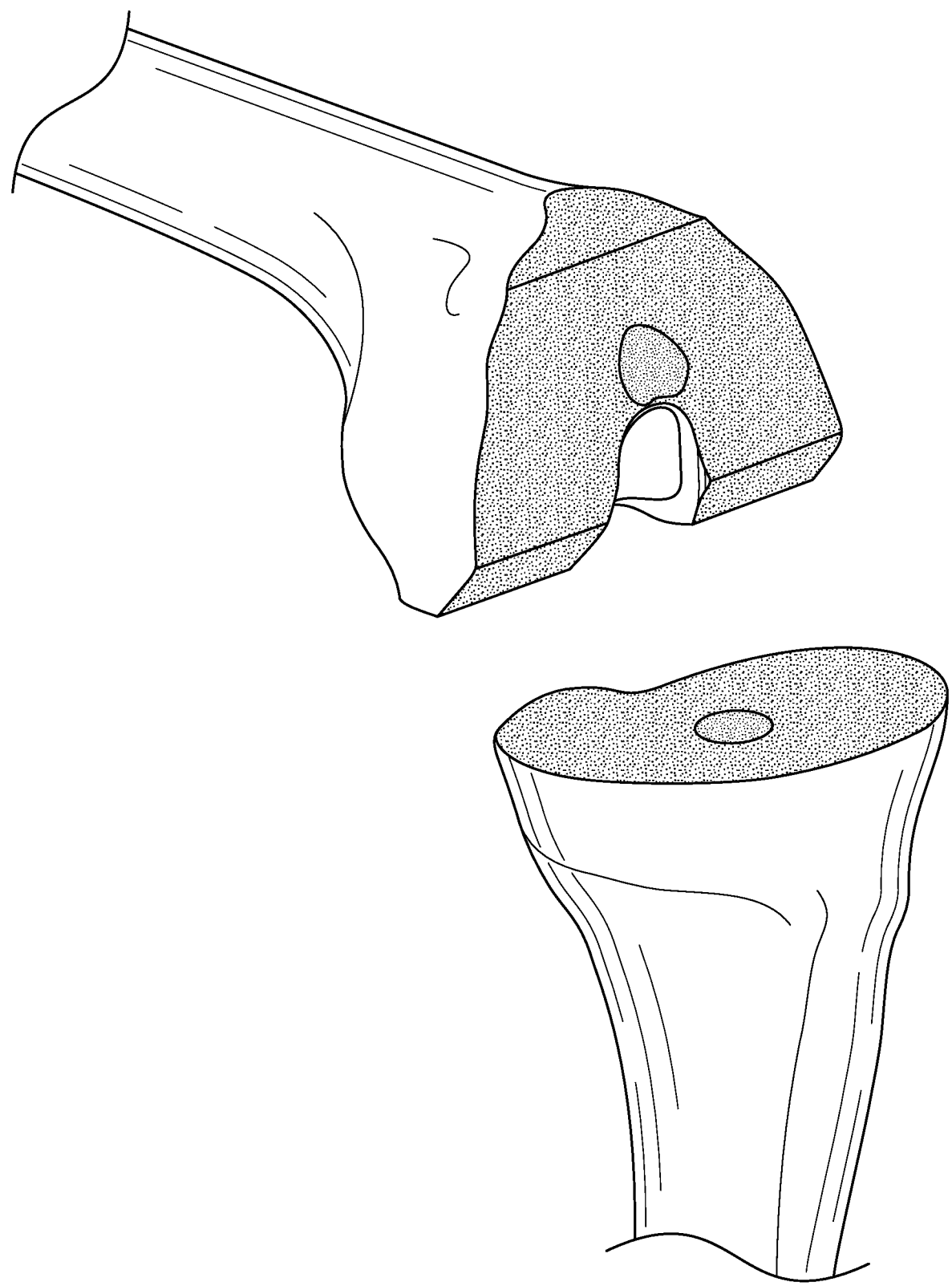
FIG. 13 shows a femur and tibia of a knee joint after the tibia and femur have been prepared.
Figure 14:
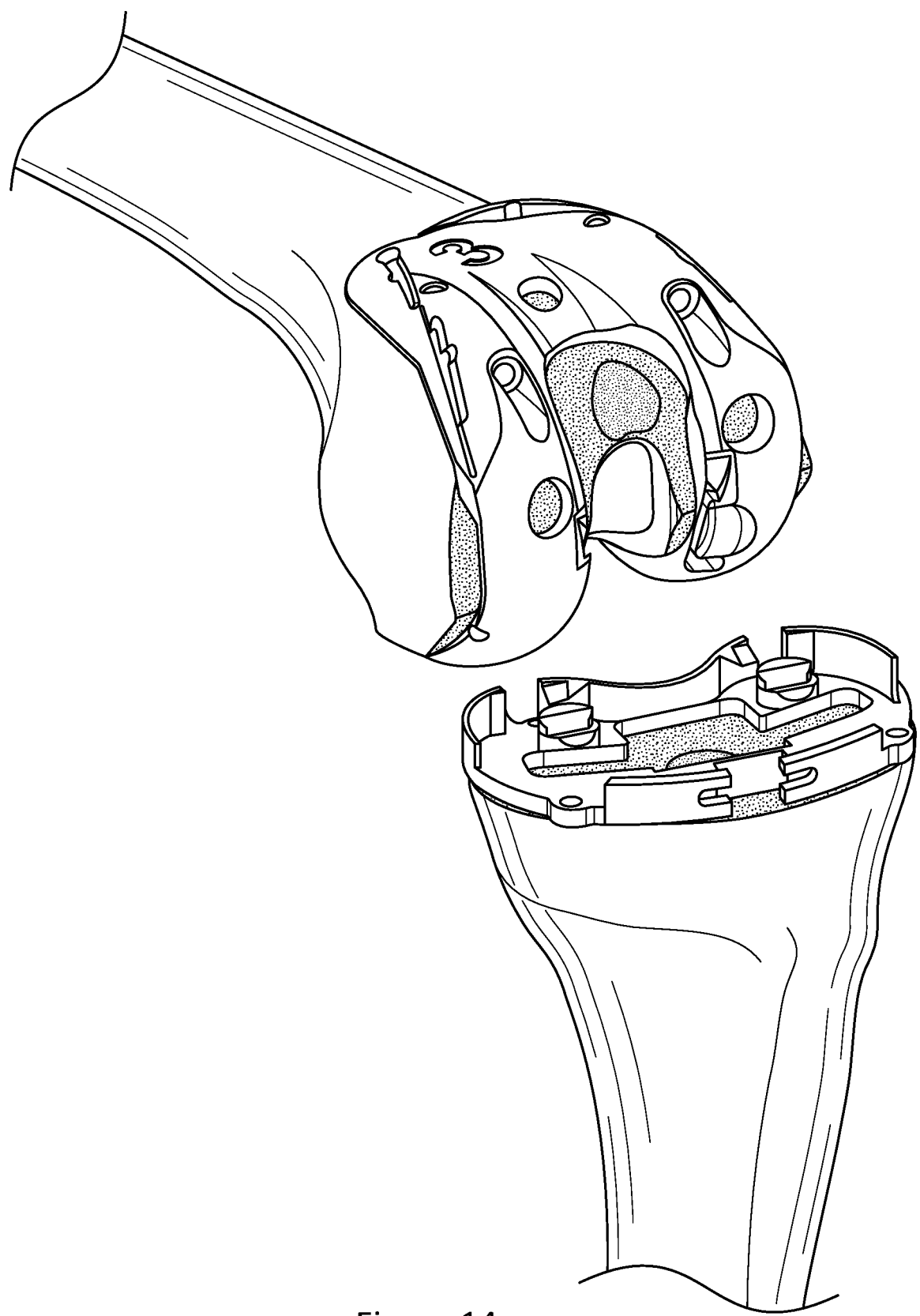
FIG. 14 shows the knee joint of FIG. 13 after a femoral component trial and tibial baseplate trial have been installed.

Next, in some embodiments, the surgeon prepares the distal femur per the previously defined planning as discussed above. FIG. 13 shows the femur and tibia after the distal femur has been prepared in this manner. Next, in some embodiments, the surgeon places the properly sized tibial baseplate trial and femoral component trial (e.g., sized based on the size of the tibia and the femur). FIG. 14 shows the femur and tibia after receiving the tibial baseplate trial and the femoral component trial.

Next, in some embodiments, the surgeon selects one of the tibial insert trials 300 from the kit 100. In some embodiments, the surgeon selects one of the tibial insert trials 300 that is compatible with the size of both the tibial baseplate trial and the femoral component trial, and which has a thickness compatible with the joint gap defined at the planning stage. As noted above with reference to FIG. 3, the selected tibial insert trial 300 includes recesses 310 configured to receive the selected sensors 400, which were previously used with the distractor 200 as described above. In some embodiments, the surgeon assembles the sensors 400 with the selected tibial trial insert 300. FIG. 15A shows a top view and cross-sectional view of one of the tibial insert trials 300 before assembly. FIG. 15B shows a top view and cross-sectional view of one of the tibial insert trials after having two of the sensors 400 assembled therewith. FIG. 15C shows a perspective rendering of one of the tibial insert trials 300 and two of the sensors 400 before assembly. FIG. 15D shows a cross-sectional rendering of the one of the tibial insert trials 300 and sensors 400 of FIG. 15C. FIG. 15E shows the view of FIG. 15D after the sensors 400 have been assembled with the one of the tibial insert trials 300.

Figure 16:
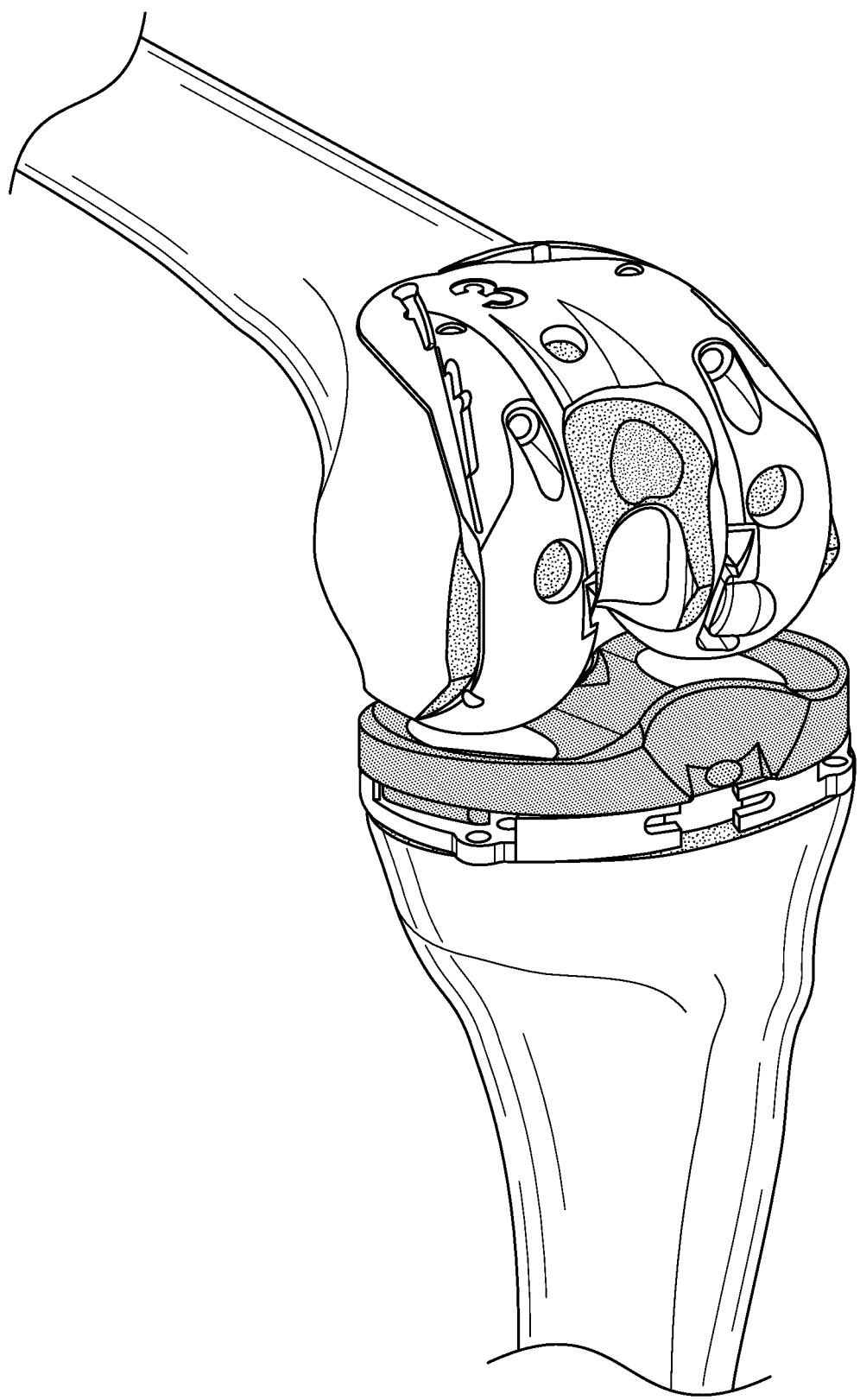
FIG. 16 shows the knee joint of FIG. 14, after an assembled tibial trial insert with sensors has been placed in the tibial baseplate trial.

Next, in some embodiments, the surgeon places the assembled tibial insert trial 300 (i.e., including the at least one sensor 400) into the space in the tibial baseplate trial in order to verify the proper balancing of the knee joint as well as the preferred thickness of the tibial insert implant to be used. FIG. 16 shows the assembled tibial trial 300 and the at least one sensor 400 as inserted into the tibial baseplate trial. This use of the sensors 400 and the data recorded thereby is referred to herein as the "verification stage". In some embodiments, if the load recorded by the at least one sensor 400 during this stage is lower than expected, then the surgeon may select a thicker one of the tibial insert trials 300 and repeat the verification stage. Similarly, in some embodiments, if the load recorded by the at least one sensor 400 during this stage is higher than expected, then the surgeon may select a thinner one of the tibial insert trials 300 and repeat the verification stage. In some embodiments, in case of slight discrepancy in term of balancing (e.g., the load recorded by the at least one sensor 400 that is to the medial side of the tibial insert trial 300 higher than the load recorded by the at least one sensor 400 that is to the lateral side of the tibial insert trial 300), then surgeon may elect to perform a slight ligament release.

Next, in some embodiments, the surgeon places the final femoral component and tibial baseplate implants. In some embodiments, the surgeon may elect to perform a secondary verification stage with the final implants in place. In order to do so, the surgeon places the assembled tibial insert trial (i.e., the selected one of the tibial insert trials 300 assembled with the at least one sensor 400) into the knee joint in order to verify the proper balancing of the knee joint as well as the preferred thickness of the tibial insert to be used. In some embodiments, the information from the sensor can be used to manage the thickness of the cement mantle during the cementation polymerization. Last, in some embodiments, surgeon places the final tibial insert implant and closes the knee joint.

While the present document discloses an application of the proposed method and instrumentation kit to a TKA, it will be apparent to those of skill in the art that this approach can be applied to other applications. In some embodiments, a third sensor-based device can be used in the patella-femoral joint in order to provide guidance regarding the level of soft-tissue tension. In some embodiments, the exemplary method and kit can be applied to a unicondylar knee arthroplasty. In such an embodiment, the mechanical distractor may be configured to only distract one compartment of the knee joint, and only one sensor may be used (instead of two sensors as discussed above). The exemplary embodiments described herein are described with specific reference to the knee joint. However, the broader principles of this disclosure can apply to any other joints (e.g., ankle, hip, elbow, shoulder) that may benefit from the proposed improvements by, for example, changing "tibia" and "femur" to "first bone" and "second bone", respectively.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated). All publications and other references mentioned herein are incorporated by reference in their entirety, as if each individual publication or reference were specifically and individually indicated to be incorporated by reference.

Publications and references cited herein are not admitted to be prior art.

What is claimed is:

1. A method comprising:
   positioning at least one sensor in a first member of a distractor,
      wherein the distractor is configured to separate a first bone of a joint from a second bone of the joint,
      wherein the distractor comprises the first member and a second member,
         wherein the first member includes a first side portion and a second side portion,
         wherein the first member is movable with respect to the second member to thereby separate the first bone from the second bone, and
      wherein the at least one sensor is configured to record a magnitude of a force;
   positioning the first member and the second member of the distractor between a first bone of a joint of a patient and a second bone of the joint of the patient so as to position the sensor in an intraarticular location between the first bone of the patient and the second bone of the patient;
   moving the joint of the patient through a range of flexion while the distractor applies a force so as to move the first bone of the joint of the patient away from the second bone of the joint of the patient;
   removing the first member and the second member of the distractor from the joint of the patient;
   removing the at least one sensor from the first member of the distractor;
   positioning the at least one sensor in a trial implant;
   positioning the trial implant on a resected surface of one of the first bone or the second bone of the joint of the patient;
   moving the joint of the patient through a range of flexion while the trial implant having the at least one sensor positioned therein is positioned on the resected surface of one of the first bone or the second bone of the joint of the patient; and
   verifying proper balance of the joint based on data recorded by the at least one sensor.

2. The method of claim 1, wherein the step of positioning the at least one sensor in the first member of the distractor comprises positioning a first one of the at least one sensor in the first side portion of the first member positioning a second one of the at least one sensor in the second side portion of the first member.

3. The method of claim 1, wherein the step of positioning the at least one sensor in the trial implant comprises positioning at least two sensors in the trial implant.

4. The method of claim 3, wherein a first one of the at least two sensors is positioned in the trial implant at a location corresponding to a first condyle of the first bone of the joint of the patient, and wherein a second one of the at least two sensors is positioned in the trial implant at a location corresponding to a second condyle of the first bone of the joint of the patient.

5. The method of claim 1, wherein the step of positioning the first member and the second member of the distractor between a first bone of a joint of a patient and a second bone of the joint of the patient so as to position the sensor in an intraarticular location between the first bone of the patient and the second bone of the patient comprises positioning a first one of the at least one sensor at a location corresponding to a first condyle of the first bone of the joint of the patient and positioning a second one of the at least one sensor at a location corresponding to a second condyle of the first bone of the joint of the patient.

6. The method of claim 1, wherein the trial implant is selected from a kit having a plurality of differently sized trial implants.

7. The method of claim 6, wherein each of the plurality differently sized trial implants of the kit is configured to receive the at least one sensor.

8. The method of claim 1, wherein the at least one sensor comprises a variable sensor that is configured to provide a linear relationship between the magnitude of the force and a sensor output signal.

9. The method of claim 1, wherein the at least one sensor is further configured to record at least one of a pressure mapping or a location of application of the force.

10. The method of claim 1, wherein the at least one sensor is configured to wirelessly transmit data recorded by the at least one sensor to a computing device.

11. The method of claim 10, the computing device is a computer-assisted orthopedic surgery system.

12. The method of claim 1,
wherein a first distance between the first side portion of the first member and the second member is adjustable in a range of between 5 mm and 19 mm,
wherein a second distance between the second side portion of the first second side member is adjustable in a range of between 5 mm and 19 mm,
and wherein adjustment of the first distance and adjustment of the second distance are independent of one another.

13. The method of claim 1,
wherein the distractor includes a first recess within the first side portion of the first member configured to receive a first one of the at least one sensor and a second recess within the second side portion of the first member configured to receive a second one of the at least one sensor, and
wherein each of the first and second recesses is configured to receive the corresponding one of the first and second ones of the at least one sensor in a plurality of positions, whereby a distance between the first one of the at least one sensor and the second one of the at least one sensor can be adjusted.

14. The method of claim 1, wherein the at least one sensor has a proximal aspect that is contoured so as to resemble a native articular surface and a distal aspect that is configured to be selectively received in the distractor or one of the plurality of trial elements.

15. The method of claim 14, wherein the distal aspect has a shape that is one of a diamond, a square, a rectangle, an oblong shape, an ellipse, or an elongated freeform shape.

16. The method of claim 1, further comprising:
attaching a baseplate to the resected surface of the one of the first bone or the second bone of the joint of the patient,
wherein the step of positioning the trial implant on the resected surface of the one of the first bone or the second bone of the joint of the patient comprises positioning the trial implant on the baseplate.

17. The method of claim 1, wherein the joint is a knee joint.

18. The method of claim 17, wherein the first bone is a femur, and wherein the second bone is a tibia.

* * * * *